(12) United States Patent
Koch et al.

(10) Patent No.: US 6,288,073 B1
(45) Date of Patent: Sep. 11, 2001

(54) ACRONYCINE DERIVATIVES, PREPARATION METHOD AND PHARMACEUTICAL COMPOSITIONS

(75) Inventors: Michel Koch, La Celle Saint Cloud; François Tillequin; Sylvie Michel, both of Paris; Ghanem Atassi, Saint Cloud; Alain Pierre, Les Alluets le Roi; Bruno Pfeiffer, Saint Leu la Foret; Pierre Renard, Le Chesnay, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/581,853

(22) PCT Filed: Dec. 18, 1998

(86) PCT No.: PCT/FR98/02785

§ 371 Date: Jun. 19, 2000

§ 102(e) Date: Jun. 19, 2000

(87) PCT Pub. No.: WO99/32491

PCT Pub. Date: Jul. 1, 1999

(30) Foreign Application Priority Data

Dec. 19, 1997 (FR) .................................................. 97 16131

(51) Int. Cl.[7] ................. A61K 31/4741; C07D 491/052; C07D 491/153; A61P 35/00
(52) U.S. Cl. ................... 514/279; 514/230.8; 514/232.8; 514/211.09; 514/280; 544/99; 544/125; 540/455; 540/521; 546/41; 546/47
(58) Field of Search ........................ 546/41, 47; 544/125, 544/99; 540/455, 521; 514/279, 280, 232.8, 230.8, 211.09

(56) References Cited

U.S. PATENT DOCUMENTS 5,567,707 * 10/1996 Koch ..................................... 514/280

OTHER PUBLICATIONS

Elomri A et al. J. Med. Chem. 1996, 39(24), 4762–4764.*
A. Elomri et al., "Synthesis and Cytotoxic and Antitumor Activity of Esters in the 1,2–Dihydroxy–1,2–Dihydroacronycine Series", Journal of Medicinal Chemistry, vol. 39, No. 24 (1996) pp. 4762–4764.

* cited by examiner

Primary Examiner—Evelyn Mei Huang
(74) Attorney, Agent, or Firm—The Firm of Hueschen and Sage; G. Patrick Sage

(57) ABSTRACT

A compound selected from those of formula (I):

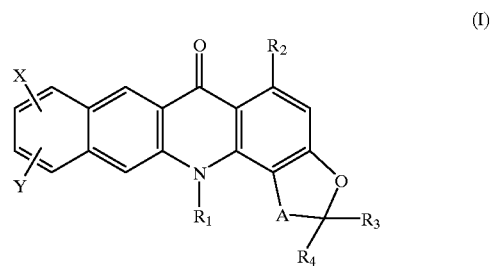

in which:
X and Y represent hydrogen, halogen, hydroxy, mercapto, cyano, nitro, alkyl, alkoxy, trihaloalkyl, optionally substituted amino, methylenedioxy, or ethylenedioxy,
$R_1$ represents hydrogen, or alkyl,
$R_2$ represents hydrogen, hydroxy, alkyl, alkoxy, alkylcarbonyloxy, or optionally substituted ammo,
$R_3$ and $R_4$ represent hydrogen, or alkyl,
A represents —CH=CH—, or —CH($R_5$)—CH($R_6$)— wherein $R_5$ and $R_6$ are as defined in the description,
their isomers, N-oxides, and pharmaceutically-acceptable acid or base addition salts thereof,
and medicinal products containing the same which are useful in the treatment of cancer.

12 Claims, No Drawings

ACRONYCINE DERIVATIVES, PREPARATION METHOD AND PHARMACEUTICAL COMPOSITIONS

The present application is a U.S. National Application filed under 35 USC 371 of PCT/FR98/02785 filed Dec. 18, 1998 based upon French application Serial No. 97.16131 filed Dec. 19, 1997.

FIELD OF THE INVENTION

The present invention relates to new acronycine compounds and to pharmaceutical compositions containing them.

Acronycine is an alkaloid having anti-tumour properties which have been demonstrated in experimental models (*J. Pharmacol. Sci.* 1966, 55 (8), 758–768). However, despite a broad spectrum of activity, the poor solubility of acronycine limits its bioavailability and does not allow for the possibility of its use in an injectable form of administration.

Various chemical modifications have been carried out on that molecule, such as those described in the article *J. Med. Chem.* 1996, 39 4762–4766, and have allowed the problem of the solubility of the compounds to be solved to some extent.

The compounds of the invention, as well as being new, have valuable solubilisation properties which are suited to administration of the compounds in liquid form and, surprisingly, they also exhibit an activity in vitro and in vivo which is far superior to that observed hitherto. Accordingly, the new analogues, discovered by the Applicants, have anti-tumour properties which render them especially suitable for use in the treatment of cancers and, especially, of solid tumours.

DETAILED DESCRIPTION OF THE INVENTION

The present invention relates more particularly to compounds of formula (I):

in which:
X and Y, which may be identical or different, each independently of the other represents a hydrogen atom, a halogen atom, a hydroxy group, a mercapto group, a cyano group, a nitro group, a linear or branched $(C_1-C_6)$alkyl group, a linear or branched $(C_1-C_6)$ alkoxy group, a linear or branched $(C_1-C_6)$trihaloalkyl group, an amino group (optionally substituted by one or two identical or different linear or branched $(C_1-C_6)$ alkyl groups which are themselves optionally substituted by a linear or branched $(C_1-C_6)$alkoxy group or by a group of the formula $-NR_7R_8$ wherein $R_7$ and $R_8$, which may be identical or different, each independently of the other represents a hydrogen atom or a linear or branched $(C_1-C_6)$alkyl group), or X and Y together form a methylenedioxy group or an ethylenedioxy group, $R_1$ represents a hydrogen atom or a linear or branched $(C_1-C_6)$alkyl group, $R_2$ represents:
  a hydrogen atom,
  a hydroxy group,
  a linear or branched $(C_1-C_6)$alkyl group,
  a linear or branched $(C_1-C_6)$alkoxy group which is optionally substituted:
    by a group of the formula $NR_7R_8$ wherein $R_7$ and $R_8$, which may be identical or different, each independently of the other represents a hydrogen atom, a linear or branched $(C_1-C_6)$alkyl group or a linear or branched $(C_1-C_6)$ hydroxyalkyl group,
    or by a saturated or unsaturated, monocyclic or bicyclic heterocycle having from 5 to 7 ring members and containing one or two hetero atoms selected from oxygen, nitrogen and sulphur,
  a linear or branched $(C_1-C_6)$alkylcarbonyloxy group,
  or an amino group which is optionally substituted:
    by one or two identical or different linear or branched $(C_1-C_6)$alkyl groups,
    by a linear or branched $(C_1-C_6)$alkylcarbonyl group which is eventually substituted by a group of the formula $NR_7R_8$ wherein $R_7$ and $R_8$ are as defined above,
    by a group of the formula $-R_9-NR_7R_8$ wherein $R_9$ represents a linear or branched $(C_1-C_6)$alkylene group and $R_7$ and $R_8$, which may be identical or different, each independently of the other represents a hydrogen atom, a linear or branched $(C_1-C_6)$alkyl group or a linear or branched $(C_1-C_6)$hydroxyalkyl group,
    by a linear or branched $(C_1-C_6)$alkylene group which is substituted by a saturated or unsaturated, monocyclic or bicyclic heterocycle having from 5 to 7 ring members and containing one or two hetero atoms selected from oxygen, nitrogen and sulphur,
    or by a group of the formula $$R_9-\underset{\underset{O}{\|}}{C}-R_{10}$$

wherein $R_9$ is as defined above and $R_{10}$ represents a hydroxy group or a linear or branched $(C_1-C_6)$alkoxy group, $R_3$ and $R_4$, which may be identical or different, each independently of the other represents a hydrogen atom or a linear or branched $(C_1-C_6)$alkyl group, A represents a $-CH=CH-$ group or an ethylene group of the formula $-CH(R_5)-CH(R_6)$ wherein $R_5$ and $R_6$, which may be identical or different, each independently of the other represents:
  a hydrogen atom,
  a hydroxy group,
  a linear or branched $(C_1-C_6)$alkoxy group,
  a linear or branched $(C_1-C_6)$alkylcarbonylexy group,
  an arylcarbonyloxy group,
  an amino group optionally substituted by one or two identical or different linear or branched $(C_1-C_6)$alkyl groups or by a linear or branched $(C_1-C_6)$acyl group, a mercapto group, a linear or branched $(C_1-C_6)$ alkylthio group or an arylthio group, or $R_5$ and $R_6$ together form:

-a

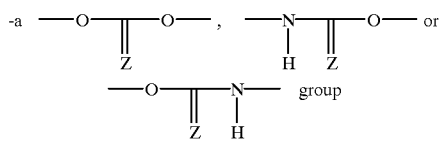

wherein Z represents an oxygen atom or a sulphur atom, a —O—$(CH_2)_n$—O— group wherein n is an integer from 1 to 4 inclusive, -a 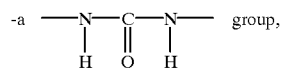 group, or a

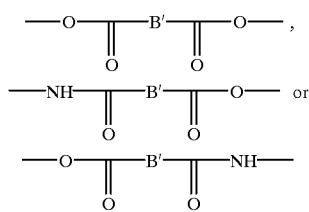

group wherein B' represents a single bond, a linear or branched $(C_1-C_6)$alkylene group or a linear or branched $(C_1-C_6)$alkenylene group, or $R_5$ and $R_6$ form together with the carbon atoms carrying them an oxirane group or an aziridine group, optionally substituted on the nitrogen atom by a linear or branched $(C_1-C_6)$alkyl group, wherein the term "aryl" denotes a phenyl or naphthyl group optionally containing one or more identical or different substituents selected from hydroxy, halogen, carboxy, nitro, amino, linear or branched $(C_1-C_6)$alkylamino, linear or branched di-$(C_1-C_6)$alkylamino, linear or branched $(C_1-C_6)$ alkoxy, linear or branched $(C_1-C_6)$acyl and linear or branched $(C_1-C_6)$alkylcarbonyloxy, their isomers, N-oxides, and addition salts thereof with a pharmaceutically acceptable acid or base.

Of the pharmaceutically acceptable acids there may be mentioned by way of non-limiting examples hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Of the pharmaceutically acceptable bases there may be mentioned by way of non-limiting examples sodium hydroxide, potassium hydroxide, triethylamine, tert-butylamine, etc.

The preferred substituents $R_3$ and $R_4$ according to the invention are linear or branched $(C_1-C_6)$alkyl groups, with $R_3$ and $R_4$ being identical or different.

The preferred substituents $R_2$ according to the invention are linear or branched $(C_1-C_6)$alkoxy groups, or amino groups optionally substituted by one or two substituents as defined above, and advantageously amino groups substituted by a group of the formula —$R_9$—$NR_7R_8$ wherein $R_9$ is as defined above, and $R_7$ and $R_8$, which may be identical or different, represents a hydrogen atom or a linear or branched $(C_1-C_6)$alkyl group.

Advantageously, the preferred compounds of the invention are those of formula (I) in which A represents a —CH=CH— group or a group of the formula —CH($R_5$)—CH($R_6$)— wherein $R_5$ and $R_6$ represent a hydroxy group or a linear or branched $(C_1-C_6)$alkylcarbonyloxy or $R_5$ and $R_6$ together form a

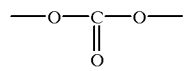

group.

Especially advantageously, the preferred compounds of the invention are the compounds of formula (I) which are:

- (±)cis-1,2-diacetoxy-6-methoxy-3,3,14-trimethyl-2,3,7,14-tetrahydro-1H-benzo[b]pyrano[3,2-h]-acridin-7-one,
- cis-7-methoxy-4,4,15-trimethyl-3a,8,15,15c-tetrahydro-4H-benzo[b][1,3]dioxolo[4',5':4,5]pyrano[3,2-h]acridine-2,8-dione,
- 6-methoxy-3,3,14-trimethyl-7,14-dihydro-3H-benzo[b]pyrano[3,2-h]acridin-7-one,
- 6-(diethylaminopropylamino)-3,3,14-trimethyl-7,14-dihydro-3H-benzo[b]pyrano[3,2-h]acridin-7-one,
- (±)-cis-diacetoxy-6-(diethylaminopropylamino)-3,3,14-trimethyl-2,3,7,14-tetrahydro-1H-benzo[b]pyrano[3,2-h]acridin-7-one.

The isomers, N-oxides and, where appropriate, the addition salts with a pharmaceutically acceptable acid or base of the preferred compounds form an integral part of the invention.

The present invention extends also to a process for the preparation of compounds of formula (I), characterised in that:

either a 3-amino-2-naphthalenecarboxylic acid compound (II):

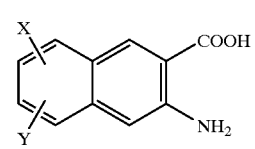

in which X and Y are as defined in formula (I), is reacted with a phloroglucinol compound of formula (III):

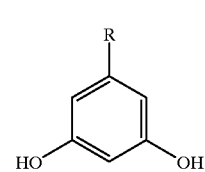

in which R represents a hydrogen atom, a hydroxy group or a linear or branched $(C_1-C_6)$alkyl group, to yield a compound of formula (IV):

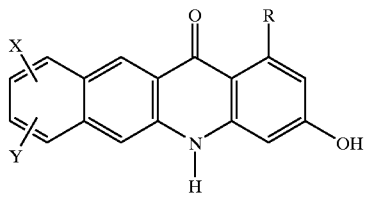

(IV)

in which X, Y and R are as defined above, which is then treated under basic conditions in an aprotic solvent, such as dimethylformamide, with an alkyne of formula (V):

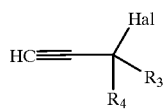

(V)

in which Hal represents a halogen atom and $R_3$ and $R_4$ are as defined in formula (I),
to yield a compound of formula (I/a), a particular case of the compounds of formula (I):

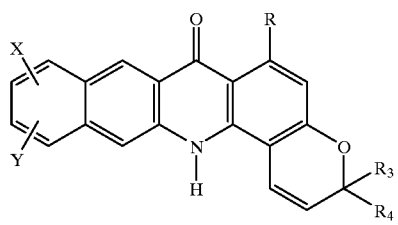

(I/a)

in which X, Y, R, $R_3$ and $R_4$ are as defined above,
or a 3-halo-2-naphthalenecarboxylic acid compound of formula (VI):

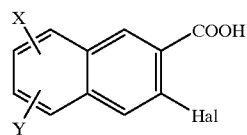

(VI)

in which X and Y are as defined in formula (I) and Hal represents a halogen atom, such as chlorine or bromine, is reacted with an amino-chromene compound of formula (VII):

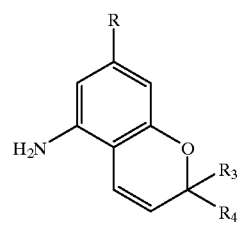

(VII)

in which $R_3$ and $R_4$ are as defined in formula (I) and R has the same meaning as above, to yield likewise a compound of formula (I/a), a particular case of the compounds of formula (I):

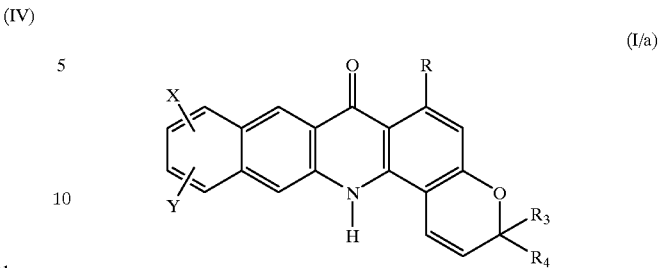

(I/a)

in which X, Y, R, $R_3$ and $R_4$ are as defined above,
in which compounds of formula (I/a)
the nitrogen atom is optionally substituted by the action of an alkyl halide or a dialkyl sulphate in the presence of a deprotonating agent, such as sodium hydride, in a polar aprotic solvent, in such a manner as to obtain a compound of formula (I/b), a particular case of the compounds of formula (I):

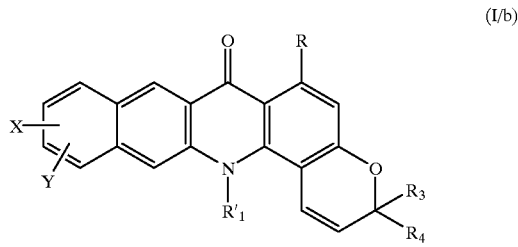

(I/b)

in which X, Y, R, $R_3$ and $R_4$ are as defined above and $R'_1$ represents a linear or branched $(C_1-C_6)$alkyl group,
which compound of formula (I/b)
may be subjected to the action of an alkylating agent, such as a dialkyl sulphate, of an acylating agent, such as acetic anhydride, or may be treated under Friedel-Crafts reaction conditions to yield a compound of formula (I/c), a particular case of the compounds of formula (I):

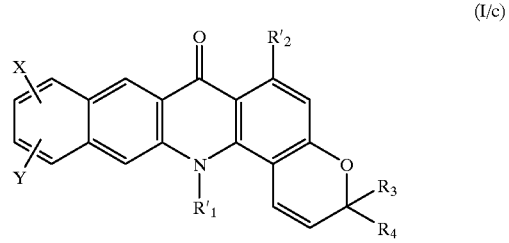

(I/c)

in which X, Y, $R'_1$, $R_3$ and $R_4$ are as defined above and $R'_2$ represents an alkoxy group optionally substituted by a group of the formula $NR_7R_8$ as defined in formula (I), or $R'_2$ represents linear or branched $(C_1-C_6)$alkylcarbonyloxy,
which compound of formula (I/c)
may optionally be treated, when $R'_2$ represents an alkoxy group, for example, with an amino compound of formula (VIII):

$HNR_aR_b$ (VIII)

in which $R_a$ represents a hydrogen atom or a linear or branched $(C_1-C_6)$alkyl group and $R_b$ represents an alkyl group, a R₉—NR₇R₈ group (wherein R₉ represents a linear or branched (C₁-C₆)alkylene group and R₇ and R₈, which may be identical or different, represent a hydrogen atom, a linear or branched (C₁-C₆)alkyl group, or a linear or branched (C₁-C₆)hydroxyalkyl group), a heterocycloalkylene group (wherein the terms alkylene and heterocycle have the same meaning as in formula (I)), or a

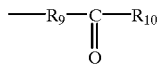

wherein R₉ and R₁₀ are as defined in formula (I),
to yield a compound of formula (I/d), a particular case of the compounds of formula (I):

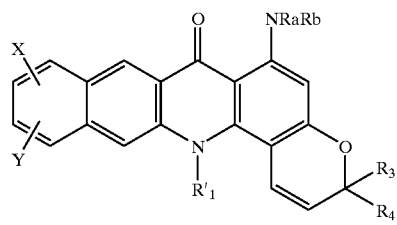

(I/d)

in which X, Y, R'₁, R₃, R₄, Ra and Rb are as defined above, the totality of the compounds of formulae (I/a) to (I/d) forming the compound of formula (I/e):

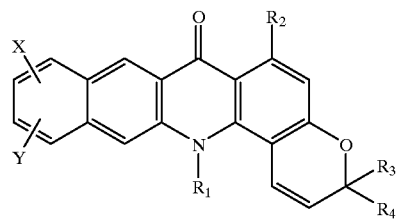

(I/e)

in which X, Y, R₁, R₂, R₃ and R₄ have the same meaning as in the general definition of formula (I),
which compound of formula (I/e) may be subjected
  a) either to the action of a reducing agent to yield a compound of formula (I/f), a particular case of the compounds of formula (I):

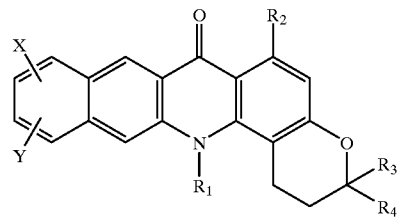

(I/f)

in which X, Y, R₁, R₂, R₃ and R₄ are as defined above,
  b) or to the action of osmium tetroxide in a polar medium and in the presence of 4-methylmorpholine N-oxide, to yield the compounds of formulae (I/g) and (I/g'), which are particular cases of the compounds of formula (I):

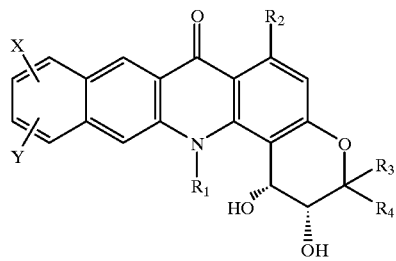

(I/g)

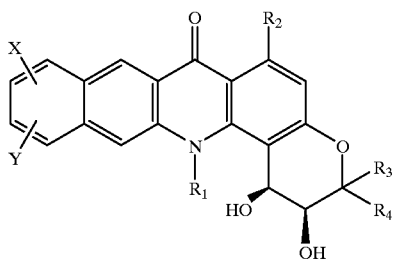

(I/g')

in which X, Y, R₁, R₂, R₃ and R₄ are as defined above, which compounds of formulae (I/g) and (I/g') may also be obtained separately by chiral synthesis and, especially, by asymmetric cis dihydroxylation starting from a compound (I/e) using chiral ligands of the pyridine or phthalazine type disubstituted by cinchona alkaloids, such as dihydroquinine and its dextrorotatory diastercoisomer dihydroquinidine, the totality of the compounds of formulae (I/g) and (I/g') forming the cis-diol compounds of formula (cis-I/h):

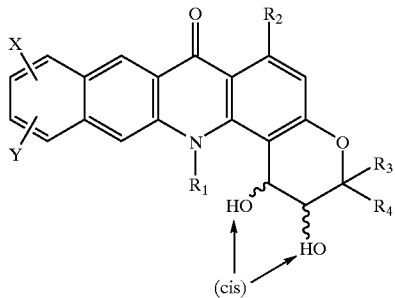

(cis-I/h)

in which X, Y, R₁, R₂, R₃ and R₄ are as defined above, which cis-diol compounds of formula (cis-I/h) are optionally subjected to the action of N,N'-carbonyldiimidazole or N,N'-thiocarbonyldiimidazole in the presence of 2-butanone to yield a compound of formula (cis-I/i), a particular case of the compounds of formula (I):

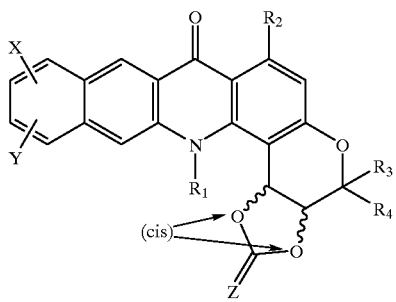

(cisI/i)

in which X, Y, $R_1$, $R_2$, $R_3$ and $R_4$ are as defined above and Z represents an oxygen atom or a sulphur atom, c) or to the action of potassium permanganate in a polar medium to yield a compound of formula (IX):

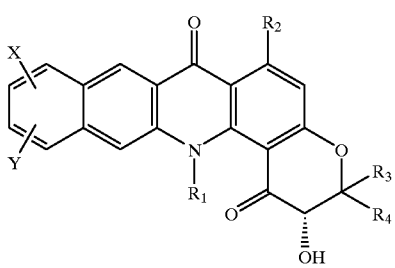

(IX)

in which X, Y, $R_1$, $R_2$, $R_3$ and $R_4$ are as defined above, which is subjected to reducing conditions in the presence of $NaBH_4$, for example, to yield a compound of formula (I/j), a particular case of the compounds of formula (I):

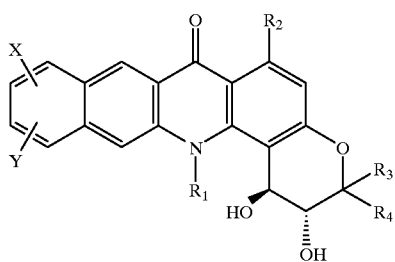

(I/j)

in which X, Y, $R_1$, $R_2$, $R_3$ and $R_4$ are as defined above, the totality of the compounds of formulae (I/j) and (cis-I/h) forming the compounds of formula (I/k):

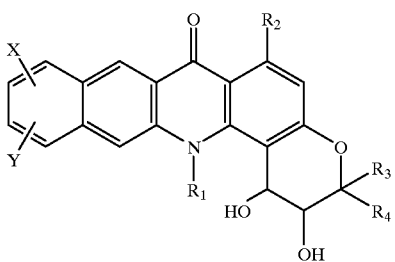

(I/k)

in which X, Y, $R_1$, $R_2$, $R_3$ and $R_4$ are as defined above, which compounds of formula (I/k) are subjected:

either to the action of a compound of formula (X) or (XI):

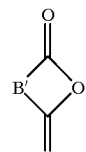

(X)

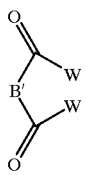

(XI)

in which B' is as defined in formula (I) and W represents a halogen atom or a hydroxy group, to yield a compound of formula (I/l):

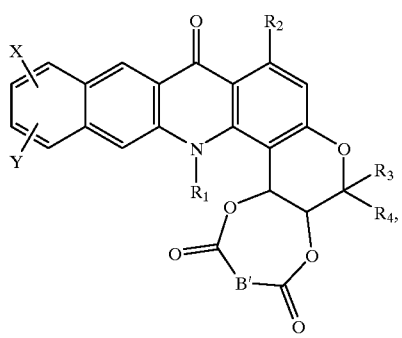

(I/l)

which is a particular case of the compounds of formula (I) in which B', X, Y, $R_1$, $R_2$, $R_3$ and $R_4$ are as defined above, or to the action of a linear $(C_1-C_6)$alkyl dihalide to yield a compound of formula (I/m), a particular case of the compounds of formula (I):

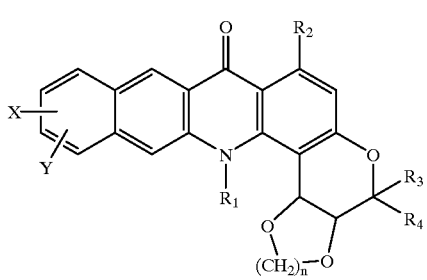

(I/m)

in which X, Y, $R_1$, $R_2$, $R_3$, $R_4$ and n are as defined above, or to the action of an alcohol of the formula $R_{11}$—OH wherein $R_{11}$ represents a linear or branched $(C_1-C_6)$ alkyl group, to yield a compound of formula (I/n):

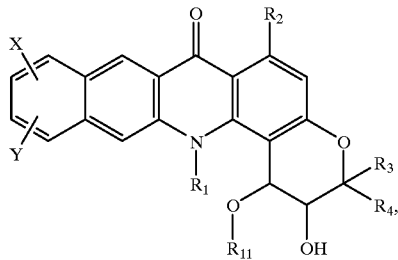

which is a particular case of the compounds of formula (I) in which X, Y, $R_1$, $R_2$, $R_3$, $R_4$ and $R_{11}$ are as defined above, the alcohol function of which compound of formula (I/n) is esterified in the presence of a weak base, such as pyridine, by an anhydride of the formula $(R_{12}CO)_2O$ wherein $R_{12}$ represents a linear or branched $(C_1–C_6)$alkyl group or an aryl group as defined above, to yield a compound of formula (I/o), a particular case of the compounds of formula (I):

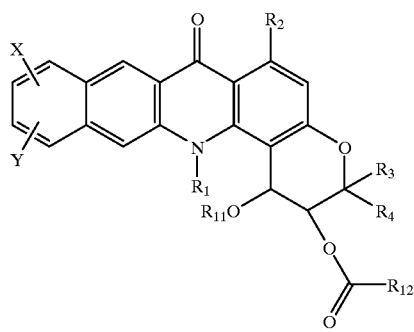

in which X, Y, $R_1$, $R_2$, $R_3$, $R_4$, $R_{11}$ and $R_{12}$ are as defined above, or to the action of an alkyl iodide of the formula $R'_{11}$-I wherein $R'_{11}$ represents a linear or branched $(C_1–C_6)$ alkyl group, in the presence of silver salt, to yield a compound of formula (I/p):

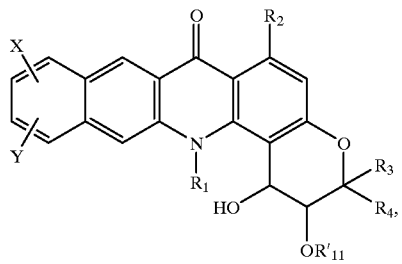

which is a particular case of the compounds of formula (I) in which X, Y, $R_1$, $R_2$, $R_3$, $R_4$ and $R'_{11}$ are as defined above, the alcohol function of which compound of formula (I/p) is esterified by an anhydride of the formula $(R'_{12}CO_2)O$ wherein $R'_{12}$ represents a linear or branched $(C_1–C_6)$alkyl group or an aryl group as defined above, to yield a compound of formula (I/q):

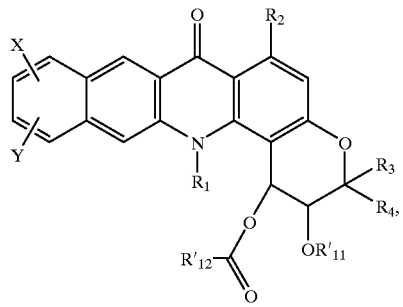

which is a particular case of the compounds of formula (I) in which X, Y, $R_1$, $R_2$, $R_3$, $R_4$, $R'_{11}$ and $R'_{12}$ are as defined above, or to the direct action of an anhydride of the formula $(R_{12}CO_2)O$ in the presence of a base, such as triethylamine, in order to obtain a compound of formula (I/r), a particular case of the compounds of formula (I):

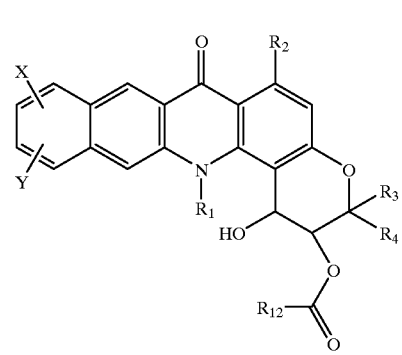

in which X, Y, $R_1$, $R_2$, $R_3$, $R_4$ and $R_{12}$ are as defined above, which may again be subjected, under the same operating conditions, to the action of the anhydride of the formula $(R'_{12}CO_2)O$ to yield a compound of formula (I/s):

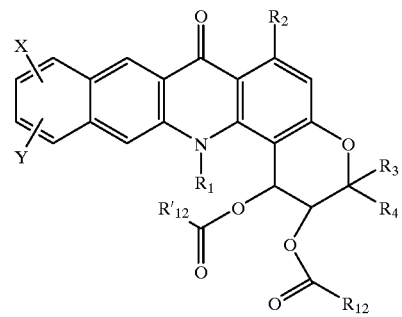

in which X, Y, $R_1$, $R_2$, $R_3$, $R_4$, $R_{12}$ and $R'_{12}$ are as defined above, the two groups $R_{12}$ and $R'_{12}$ being identical or different, or to dehydrating conditions in an acid medium to yield a compound of formula (XII):

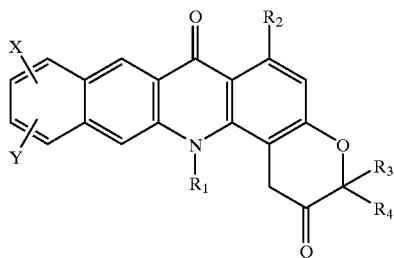

(XII)

in which X, Y, R$_1$, R$_2$, R$_3$ and R$_4$ are as defined above, which is reduced in the presence of NaBH$_4$ to yield a compound of formula (I/t):

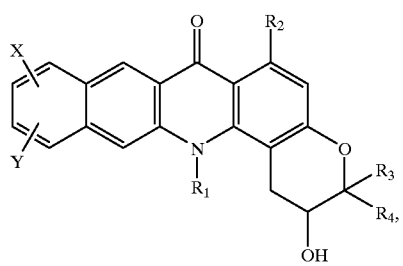

(I/t)

which is a particular case of the compounds of formula (I) in which X, Y, R$_1$, R$_2$, R$_3$ and R$_4$ are as defined above, d) or to the action of a peracid, such as m-chloroperbenzoic acid, to yield a compound of formula (I/u), a particular case of the compounds of formula (I):

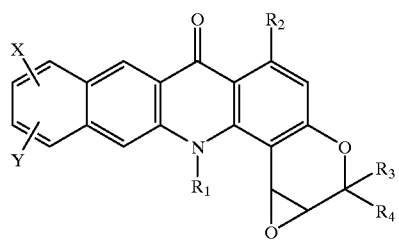

(I/u)

in which X, Y, R$_1$, R$_2$, R$_3$ and R$_4$ are as defined above, which compound of formula (I/u) is optionally treated with ammonium hydroxide or a primary or secondary amine to yield, according to the nature of the reagents, a compound of formula (I/v) and/or (I/v'), which are particular cases of the compounds of formula (I):

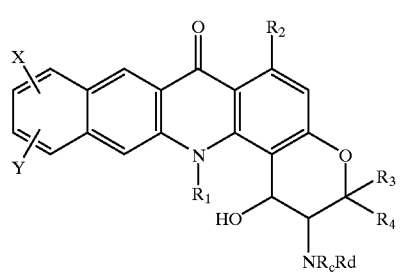

(I/v)

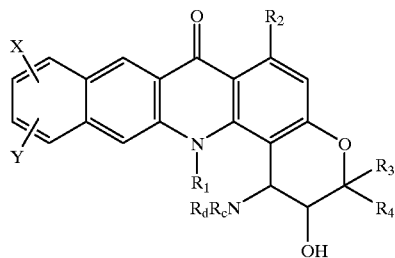

(I/v')

in which X, Y, R$_1$, R$_2$, R$_3$ and R$_4$ are as defined above and R$_c$ and R$_d$ represent a hydrogen atom or a linear or branched (C$_1$–C$_6$)alkyl group, which compound of formula (I/v') may also be obtained directly starting from a compound of formula (I/k) by treatment with NaN$_3$ to yield an intermediate azide compound, followed by hydrogenation in the presence of palladium, yielding a compound of formula (I/v') in which Rc and Rd represent a hydrogen atom, which compounds of formulae (I/v) and (I/v') may be subjected:

either, when Rc and Rd represent a hydrogen atom, to the action of N,N'-carbonyldiimidazole or N,N'-thiocarbonyldiimidazole, for example, to yield compounds of formulae (I/w) and (I/w'), respectively, which are particular cases of the compounds of formula (I):

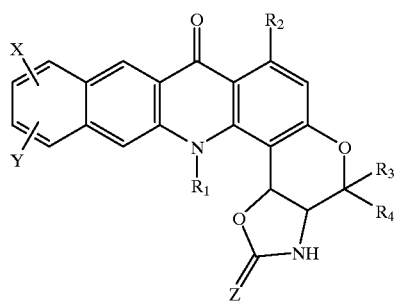

(I/w)

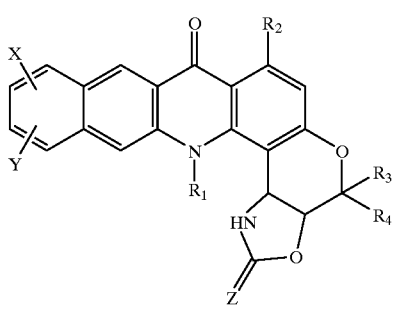

(I/w')

in which X, Y, R$_1$, R$_2$, R$_3$ and R$_4$ are as defined above and Z represents an oxygen atom or a sulphur atom, according to the nature of the reagent used, or to the action of a compound of formula (XI) WO$_2$C—B'—CO$_2$W as defined above, to yield compounds of formulae (I/x) and (I/x'), respectively, which are particular cases of the compounds of formula (I):

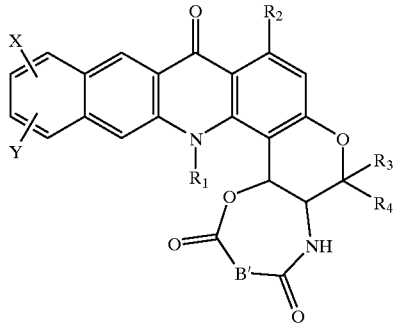

(I/x)

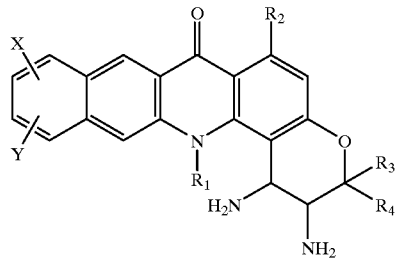

(I/z)

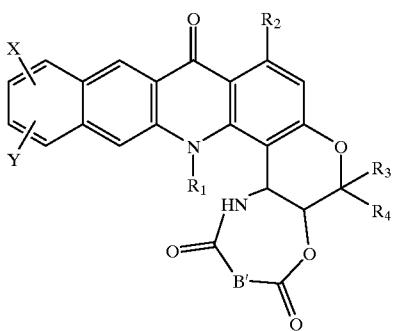

(I/x')

in which X, Y, R₁, R₂, R₃ and R₄ are as defined above, which compound of formula (I/z) may optionally be subjected to the action of carbon dioxide, in the presence of diphenyl phosphite, to yield a compound of formula (I/aa), a particular case of the compounds of formula (I):

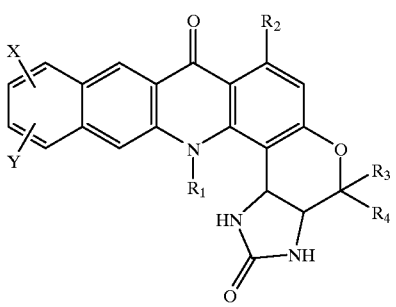

(I/aa)

in which B', X, Y, $R_1$, $R_2$, $R_3$ and $R_4$ are as defined above, or to the action of triphenylphosphine dibromide in the presence of triethylamine to yield a compound of formula (I/y), a particular case of the compounds of formula (I):

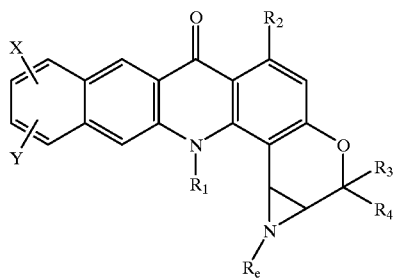

(I/y)

in which X, Y, $R_1$, $R_2$, $R_3$ and $R_4$ are as defined above and Re represents a hydrogen atom or a linear or branched ($C_1$–$C_6$)akyl group, e) or to the action of $NaN_3$ in the presence of hydrogen peroxide, followed by a reducing step by means of tri-n-butyltin hydride, for example, to yield a compound of formula (I/z), a particular case of the compounds of formula (I):

in which X, Y, $R_1$, $R_2$, $R_3$ and $R_4$ are as defined above, the compounds (I/a–z), (I/g'), (I/v'–x'), (I/aa) and (cis I/h–I/i) forming the totality of the compounds of the invention, which are purified, where appropriate, in accordance with a conventional purification technique, may, if desired, be separated into their various isomers in accordance with a conventional separating technique and, if desired, are converted into their N-oxides and, where appropriate, into their addition salts with a pharmaceutically acceptable acid or base.

The compounds of formulae (II), (III), (VI) and (VII) are either commercially available or obtained according to the conventional methods of organic synthesis and, in the case of the compounds of formula (VII), are obtained in accordance with the conditions described in *Chem. Ber.* 1978, 191, 439. The condensation reaction between the compounds of formula (VI) and the compounds of formula (VII) is described especially in the review *Heterocycles*, 1992, 34(4), 799–806.

The compounds of formula (I) have anti-tumour properties which are especially valuable. They have an excellent in vitro cytotoxicity on cell lines, and an action on the cell cycle, and they are active in vivo. Moreover, the new compounds have been found to be much more active and potent than the reference compound, acronycine. Furthermore, they have the property of being soluble, thus allowing administration by the intravenous route. The characteristic properties of those compounds allow them to be used in therapeutics as anti-tumour agents.

The present invention relates also to pharmaceutical compositions comprising as active ingredient at least one compound of formula (I), its optical isomers, N-oxides or an addition salt thereof with a pharmaceutically acceptable acid or base, on its own or in combination with one or more inert, non-toxic, pharmaceutically acceptable excipients or carriers.

Of the pharmaceutical compositions according to the invention, special mention may be made of those which are suitable for oral, parenteral (intravenous, intramuscular or subcutaneous), per- or trans-cutaneous, nasal, rectal, perlingual, ocular or respiratory administration, especially tablets, dragees, sublingual tablets, soft gelatin capsules, hard capsules, suppositories, creams, ointments, dermal gels, injectable or drinkable preparations, aerosols, ocular or nasal drops, etc.

The dosage used varies according to the age and weight of the patient, the mode of administration, the nature and severity of the disorder and the administration of any associated treatments, and ranges from 0.5 mg to 500 mg in one or more doses per day.

The Examples which follow illustrate the invention without limiting it in any way.

The starting materials used are products which are known or prepared according to known procedures.

The structures of the compounds described in the Examples and the Preparations have been determined in accordance with customary spectrophotometric techniques (infra-red, nuclear magnetic resonance, etc.).

EXAMPLE 1:

6-Hydroxy-3,3-dimethyl-7,14-dihydro-3H-benzo[b]pyrano[3,2-h]acridin-7-one

Step A: 1,3-Dihydroxy-5,12-dihydro-benzo[b]acridin-12-one 3.5 g of 1,3,5-trihydroxybenzene and 62.5 mg of para-toluenesulphonic acid are added to a solution of 5 g of 3-amino-2-naphthalenecarboxylic acid in 50 ml of heptan-1-ol. The mixture is maintained at reflux using a Dean-Stark apparatus for 48 hours, with stirring, and the reaction mixture is then concentrated in vacuo. The residue is chromatographed on silica gel (eluant: cyclohexane/acetone: 90/10). The isolated product is crystallised from a cyclohexane/acetone mixture, yielding 5.2 g of the expected product.

Step B: 6-Hydroxy-3,3-dimethyl-7,14-dihydro-3H-benzo[b]pyrano[3,2-h]acridin-7-one 2 g of anhydrous potassium carbonate are added to a solution of 2 g of the product of Step A in 50 ml of anhydrous dimethylformamide, under an inert atmosphere. After stirring for 15 minutes at 65° C., 2.4 g of anhydrous potassium iodide and 4.4 g of 3-chloro-3-nmethyl-1-butyne are added and the reaction mixture is maintained at 65° C. for 24 hours and then at 130° C. for 1 hour 30 minutes. After cooling, the solution is hydrolysed and then extracted with dichloromethane. The combined organic phases are washed with water and then with a 1M solution of potassium hydroxide, dried over sodium sulphate and then evaporated. After chromatography on silica gel (cyclohexane/acetone: 90/10), 1.10 g of the expected product are isolated.

Melting point: 225° C.

EXAMPLE 2

6-Methoxy-3,3,14-trimethyl-7,14-dihydro-3H-benzo[b]pyrano[3,2-h]acridin-7-one

Step C

To a solution of 0.5 g of the product of Example 1 in 20 ml of anhydrous dimethylformamide there are slowly added at 0° C., under an inert atmosphere, 0.16 g of sodium hydride and then, after 15 minutes, 0.65 ml of dimethyl sulphate (6 equivalents). After one hour, the reaction mixture is poured onto ice and then extracted with ethyl acetate. The organic phase is washed with an aqueous sodium hydroxide solution and subsequently dried over sodium sulphate and then evaporated in vacuo. Chromatography on silica gel (cyclohexane/acetone: 98/2) allows 0.42 g of the expected product to be isolated.

Melting point: 188° C.

EXAMPLE 3

6-Hydroxy-3,3,14-trimethyl-7,14-dihydro-3H-benzo[b]pyrano[3,2-h]acridin-7-one

The procedure of Step C of Example 2 is followed, using only 1.5 equivalents of sodium hydride and 2 equivalents of dimethyl sulphate.

Melting point: 138° C.

EXAMPLE 4

(±)-cis-1,2-Dihydroxy-4-methoxy-3,3,14-trimethyl-2,3,7,14-tetrahydro-1H-benzo[b]pyrano[3,2-h]acridin-7-one 2.5% of osmium tetroxide dissolved in 3.8 ml of 2-methyl-2-propanol are added to a solution of 2 g of the product of Example 2 and 0.9 g of 4-methylmorpholine N-oxide monohydrate in 40 ml of a tert-butanol/tetrahydrofaran/water mixture (10/3/1). After 2 days at room temperature, 105 ml of a saturated solution of $NaHSO_3$ are added and the reaction mixture is stirred for one hour and then extracted with dichloromethane. The combined organic phases are dried over sodium sulphate and concentrated in vacua. Chromatography on silica gel (dichloromethane/methanol: 95/5) allows 1.3 g of the expected product to be isolated.

Melting point: 194° C.

EXAMPLE 5

(±)-cis-1,2-Diacetoxy-4-methoxy-3,3,14-trimethyl-2,3,7,14-tetrahydro-1H-benzo[b]pyrano[3,2-h]acridin-7-one 0.33 g of the product of Example 4 is added to a cooled solution of 0.82 ml of pyridine and 0.82 ml of acetic anhydride. After 6 days at room temperature, the reaction mixture is poured onto ice. A precipitate forms and is filtered off, washed with water and then dried in vacuo. 0.36 g of the expected product is obtained.

Melting point: 163° C.

EXAMPLE 6

(±)-cis-1,2-Dibenzoyloxy-6-methoxy-3,3,14-trimethyl-2,3,7,14-tetrahydro-1H-benzo[b]pyrano[3,2-h]acridin-7-one The procedure of Example 5 is followed, using benzoic anhydride as reagent.

EXAMPLE 7 cis-7-Methoxy-4,4,15-trimethyl-3a,8,15,15c-tetrahydro-4H-benzo[b][1,3]dioxolo[4',5':4,5]pyrano[3,2-h]acridine-2,8-dione 0.24 g of N,N'-carbonyldiimidazole is added to a solution of 0.12 g of the product of Example 4 in 5 ml of 2-butanone.

After refluxing for 3 hours under argon, the reaction mixture is hydrolysed with a 5% aqueous solution of sodium carbonate and then extracted with ethyl acetate. The combined organic phases are dried over sodium sulphate and then concentrated in vacuo. Chromatography on silica gel (dichloromethane/acetone: 2/1) allows 0.75 g of the expected product to be isolated.

Melting point: 176° C.

EXAMPLE 8

6-(Dimethylaminoethylamino)-3,3,14-trimethyl-7,14-dihydro-3H-benzo[b]pyrano[3,2-h]acridin-7-one 4 ml of N,N-dimethylethylenediamine are added to 0.15 g of the product of Example 2. After reacting for 5 days at 70° C. under an inert atmosphere, the reaction mixture is evaporated under reduced pressure. The residue obtained is chromatographed on silica gel (cyclohexane/ethyl acetate: 80/20), allowing the expected product to be isolated.

Melting point: oil.

Mass spectrum: (DIC/NH$_3$): m/z: 428 (M+H)$^+$

EXAMPLE 9

6-(Dimethylaminopropylamino)-3,3,14-trimethyl-7,14-dihydro-3H-benzo[b]pyrano[3,2-h]acridin-7-one The procedure of Example 8 is followed, using N,N-dimethylpropyldiamine as reagent.

Melting point: oil.

Mass spectrum: (DIC/NH$_3$): m/z: 442 (M+H)$^+$

EXAMPLE 10

6-(Diethylaminopropylamino)-3,3,14-trimethyl-7,14-dihydro-3H-benzo[b]pyrano[3,2-h]acridin-7-one The procedure of Example 8 is followed, using N,N-diethylpropyldiamine as reagent.

Melting point: oil.

Mass spectrum: (DIC/NH$_3$): m/z: 470 (M+H)$^+$

EXAMPLE 11

6-[(3-Morpholin-4-yl)propylamino]-3,3,14-trimethyl-7,14-dihydro-3H-benzo[b]pyrano[3,2-h]acridin-7-one The procedure of Example 8 is followed, using 4-(3-aminopropyl)morpholine as reagent.

Mass spectrum: (DIC/NH$_3$): m/z: 484 (M)$^+$

EXAMPLE 12

6-[(2-Morpholin-4-yl)ethylamino]-3,3,14-trimethyl-7,14-dihydro-3H-benzo[b]pyrano[3,2-h]acridin-7-one The procedure of Example 8 is followed, using 4-(2-aminoethyl)morpholine as reagent.

Mass spectrum: (DIC/NH$_3$): m/z: 470 (M+H)$^+$

EXAMPLE 13

6-[(2-Piperidin-1-yl)ethylamino]-3,3,14-trimethyl-7,14-dihydro-3H-benzo[b]pyrano[3,2-h]acridin-7-one The procedure of Example 8 is followed, using 1-(2-aminoetbyl)piperidine as reagent Mass spectrum: (DIC/NH$_3$): m/z: 468 (M+H)$^+$

EXAMPLE 14

(±)-trans-1,2-Dihydroxy-6-methoxy-3,3,14-trimethyl-2,3,7,14-tetrahydro-1H-benzo[b]pyrano[3,2-h]acridin-7-one Step D: 1-Oxo-2-hydroxy-6-methoxy-3,3,14-trimethyl-2,3,7,14-tetrahydro-1H-benzo[b]pyrano[3,2-h]acridin-7-one A solution of 8.1 g of potassium permanganate diluted in 30 ml of water is slowly added at room temperature to a solution of 3.5 g of the product of Example 2 in 50 ml of acetone. After 2 hours, the solution is concentrated under reduced pressure. The residue is then mixed with silica and then chromatographed on silica gel (dichloromethane/methanol: 98/2), allowing the compound of Example 4, which is present in a small amount, to be isolated from the expected product.

Step E: (±)-trans-1,2-Dihydroxy-6-methoxy-3,3,14-trimethyl-2,7,14-tetrahydro-1H-benzo[b]pyrano[3,2-h]acridin-7-one 0.45 g of NaBH$_4$ is added to a solution of 1 g of the compound obtained in Step D dissolved in 30 ml of methanol. After reacting for one hour at 0° C., the reaction mixture is brought to room temperature, the solvent is evaporated off and the residue is chromatographed on silica gel (dichlorometiane/methanol: 95/5), allowing the desired product to be isolated.

EXAMPLE 15

(±)-cis-1,2-Dihydroxy-6-(dinethylaminoethylamino)-3,3,14-trimethyl-2,3,7,14-tetrahydro-1H-benzo[b]pyrano[3,2-h]acridin-7-one The procedure of Example 4 is followed, using the compound of Example 8 as substrate.

EXAMPLE 16

(±)-cis-9-Methoxy-6,6,17-trimethyl-3,4,5a,10,17,17c-hexahydro-2H,6H-benzo[b][1,4]dioxepino[2',3':4,5]pyrano[3,2-h]acridine-2,4,10-trione The procedure of Example 5 is followed, using the compound of Example 4 as substrate and acylmalonic dichloride as reagent

EXAMPLE 17 cis-7-(Dimethylaminoethylamino)-4,4,15-trimethyl-3a,8,15,15c-tetrahydro-4H-benzo[b][1,3]dioxolo[4',5':4,5]pyrano[3,2-h]acridine-2,8-dione The procedure of Example 7 is followed, using the compound of Example 15 as substrate.

EXAMPLE 18

(±)-cis-1,2-Dihydroxy-6-(dimethylaminopropylamino)-3,3,14-trimethyl-2,3,7,14-tetrahydro-1H-benzo[b]pyrano[3,2-h]acridin-7-one The procedure of Example 4 is followed, using the compound of Example 10 as substrate.

EXAMPLE 19

(±)-cis-1,2-Diacetoxy-6-(dimethylaminopropylamino)-3,3,14-trimethyl-2,3,7,14-tetrahydro-1H-benzo[b]pyrano[3,2-h]acridin-7-one The procedure of Example 5 is followed, using the compound of Example 18 as substrate.

EXAMPLE 20

(±)-cis-1-Hydroxy-2-benzoyloxy-6-methoxy-3,3,14-trimethyl-2,3,7,14-tetrahydro-1H-benzo[b]pyrano[3,2-h]acridin-7-one 0.125 g of benzoic anhydride is added to a solution of 0.2 g of the compound of Example 4 in 3 ml of pyridine. After stiring for 36 hours at room temperature, the reaction mixture is concentrated under reduced pressure. The residue is chromatographed on silica gel (eluant: ethyl acetate/toluene: 70/30).

EXAMPLE 21

(±)-cis-1-Acetoxy-2-benzoyloxy-6-methoxy-3,3,14-trimethyl-2,3,7,14-tetrahydro-1H-benzo[b]pyrano[3,2-h]acridin-7-one 2.5 ml of acetic anhydride are added to a solution of 0.1 g of the compound of Example 20 in 2.5 ml of pyridine. After reacting for 12 hours at room temperature, the reaction mixture is concentrated under reduced pressure. Chromatography on silica gel (eluant: dichloromethane) allows the expected product to be isolated.

EXAMPLE 22

(±)-1-Amino-2-hydroxy-6-methoxy-3,3,14-trimethyl-2,3,7,14-tetrahydro-1H-benzo[b]pyrano[3,2-h]acridin-7-one Step 1: (±)-1-Azido-2-hydroxy-6-methoxy-3,3,14-trimethyl-2,3,7,14-tetrahydro-1H-benzo[b]pyrano[3,2-h]acridin-7-one 3 ml of trifluoroacetic acid are slowly added at room temperature to a solution of 0.1 5 g of the compound of Example 4 and 0.5 g of $NaN_3$ in 6 ml of chloroform. After stirring for 12 hours, one equivalent of $NaN_3$ is added and the reaction is maintained at room temperature for a further 12 hours. The reaction mixture is then washed with water and then with a saturated solution of NaCl, and is dried over sodium sulfate. Chromatography on silica gel (dichloromethane/methanol: 95/5) allows the expected product to be isolated.

Step 2: (±)-1-Amino-2-hydroxy-6-methoxy-3,3,14-trimethyl-2,3,7,14-tetrahydro-1H-benzo[b]pyrano[3,2-h]acridin-7-one A solution containing 0.2 g of the compound of Step 1 and 0.09 g of Pd/C in 5 ml of ethanol is stirred at room temperature under an $H_2$ atmosphere for 48 hours. The catalyst is then filtered off and the filtrate is concentrated in vacuo. The residue is chromatographed on silica gel (dichloromethane/methanol: 95/5), allowing the desired product to be isolated.

EXAMPLE 23

7-Methoxy-4,4,15-trimethyl-1,3a,4,8,15,15c-hexahydro-2H-benzo[b][1,3]oxazolo[4',5':4,5]pyrano[3,2-h]acridine-2,8-dione The procedure of Example 7 is followed, using the compound of Example 22 as substrate.

EXAMPLE 24

6-(Diethylaminoethylamino)-3,3,14-trimethyl-7,14-dihydro-3H-benzo[b]pyrano[3,2-h]acridin-7-one The procedure of Example 8 is followed, using N,N-diethylaminoethylamine as reagent.

Mass spectrum: (DIC/$NH_3$): m/z: 456 (M+H)$^+$

EXAMPLE 25

6-(Dimethylaminoethyloxy)-3,3,14-trimethyl-7,14-dihydro-3H-benzo[b]pyrano[3,2-h]acridin-7-one One equivalent of sodium hydride and one equivalent of the hydrochloride of 2-dimethylaminoethyl chloride are added to a solution, under nitrogen, of 0.2 g of the compound of Example 3 in 20 ml of dimethylformamide. After 48 hours at 70° C., the reaction mixture is cooled and then poured onto 80 ml of ice-water and extracted with dichloromethane. After washing and drying over $MgSO_4$, the solution is evaporated under reduced pressure. Chromatography on silica gel (ethyl acetate/cyclohexane: 80/20) allows the expected product to be isolated.

Mass spectrum: (DIC/$NH_3$): m/z: 429 (M+H)$^+$

EXAMPLE 26

6-(Dimethylaminopropyloxy)-3,3,14-trimethyl-7,14-dihydro-3H-benzo[b]pyrano[3,2-h]acridin-7-one The procedure of Example 25 is followed, using the hydrochloride of 3-chloro-N,N'-dimethylpropylamine as reagent.

Mass spectrum: (DIC/$NH_3$): m/z: 443 (M+H)$^+$

EXAMPLE 27

6-(Diethylaminoethyloxy)-3,3,14-trimethyl-7,14-dihydro-3H-benzo[b]pyrano[3,2-h]acridin-7-one The procedure of Example 25 is followed, using the hydrochloride of 2-diethylaminoethyl chloride as reagent.

Mass spectrum: (DIC/$NH_3$): m/z: 457 (M+H)$^+$

EXAMPLE 28

6-[(2-Morpholin-4-yl)ethyloxy]-3,3,14-trimethyl-7,14-dihydro-3H-benzo[b]pyrano[3,2-h]acridin-7-one The procedure of Example 25 is followed, using the hydrochloride of 4-(2-chloroethyl)morpholine as reagent.

Mass spectrum: (DIC/$NH_3$): m/z: 471 (M+H)$^+$

EXAMPLE 29

6-[(Methoxycarbonyl)methylamino]-3,3,14-trimethyl-7,14-dihydro-3H-benzo[b]pyrano[3,2-h]acridin-7-one A solution containing 200 mg of the compound of Example 2 and 10 equivalents of the hydrochloride of methyl 2-aminoacetate in 15 ml of dimethylformamide is maintained at 70° C., under argon. After 3 days, the reaction mixture is concentrated under reduced pressure, and chromatography of the residue on silica gel (ethyl acetate/cyclohexane: 85/15) allows the expected product to be isolated.

Mass spectrum: (DIC/$NH_3$): m/z: 429 (M+H)$^+$

EXAMPLE 30

6-[(Ethoxycarbonyl)methylamino]-3,3,14-trimethyl-7,14dihydro-3H-benzo[b]pyrano[3,2-h]acridin-7-one The procedure of Example 29 is followed, using ethyl 2-aminoacetate as reagent.

Mass spectrum: (DIC/NH$_3$): m/z: 443 (M+H)$^+$

EXAMPLE 31

6-[(Methoxycarbonyl)propylamino]-3,3,14-trimethyl-7,14-dihydro-3H-benzo[b]pyrano[3,2-h]acridin-7-one The procedure of Example 29 is followed, using 4-aminobutyric acid as reagent, and the product so obtained is then subjected to esterification conditions in the presence of sodium methoxide.

Mass spectrum: (DIC/NH$_3$): m/z: 457 (M+H)$^+$

EXAMPLE 32

6-[(Methoxycarbonyl)butylamino]-3,3,14-trimethyl-7,14-dihydro-3H-benzo[b]pyrano[3,2-h]acridin-7-one The procedure of Example 31 is followed, using 5-aminovaleric acid as the first reagent.

EXAMPLE 33 cis-6-(Dimethylaminopropylamino)-1,2-dihydroxy-3,3,14-trimethyl-2,3,7,14-tetrahydro-1H-benzo[b]pyrano[3,2-h]acridin-7-one The procedure of Example 4 is followed, using the compound of Example 9 as substrate.

EXAMPLE 34 cis-6-[(2-Morpholin-4-yl)ethylamino]-1,2-dihydroxy-3,3,14-trimethyl-2,3,7,14-tetrahydro-1H-benzo[b]pyrano[3,2-h]acridin-7-one The procedure of Example 4 is followed, using the compound of Example 12 as substrate.

EXAMPLE 35 cis-6-[(2-Piperidin-1-yl)ethylamino]-1,2-dihydroxy-3,3,14-trimethyl-2,3,7,14-tetrahydro-1H-benzo[b]pyrano[3,2-h]acridin-7-one The procedure of Example 4 is followed, using the compound of Example 13 as substrate.

EXAMPLE 36 trans-6-(Dimethylaminoethylamino)-1,2-dihydroxy-3,3,14-trimethyl-2,3,7,14-tetrahydro-1H-benzo[b]pyrano[3,2-h]acridin-7-one The procedure of Example 14, Steps D and E, is followed, using the compound of Example 8 as substrate.

EXAMPLE 37 cis-6-(Dimethylaminoethyloxy)-1,2-dihydroxy-3,3,14-trimethyl-2,3,7,14-tetrahydro-1H-benzo[b]pyrano[3,2-h]acridin-7-one The procedure of Example 4 is followed, using the compound of Example 25 as substrate.

EXAMPLE 38 cis-6-(Dimethylaminopropyloxy)-1,2-dihydroxy-3,3,14-trimethyl-2,3,7,14-tetrahydro-1H-benzo[b]pyrano[3,2-h]acridin-7-one The procedure of Example 4 is followed, using the compound of Example 26 as substrate.

EXAMPLE 39 cis-6-[(2-Morpholin-4-yl)ethyloxy]-1,2-dihydroxy-3,3,14-trimethyl-2,3,7,14-tetrahydro-1H-benzo[b]pyrano[3,2-h]acridin-7-one The procedure of Example 4 is followed, using the compound of Example 28 as substrate.

EXAMPLE 40 cis-6-[(Methoxycarbonyl)methylamino]-1,2-dihydroxy-3,3,14-trimethyl-2,3,7,14-tetrahydro-1H-benzo[b]pyrano[3,2-h]acridin-7-one The procedure of Example 4 is followed, using the compound of Example 29 as substrate.

EXAMPLE 41 cis-6-[(Methoxycarbonyl)propylamino]-1,2-dihydroxy-3,3,14-trimethyl-2,3,7,14-tetrahydro-1H-benzo[b]pyrano[3,2-h]acridin-7-one The procedure of Example 4 is followed, using the compound of Example 31 as substrate.

EXAMPLE 42 cis-1,2-Diacetoxy-6-(dimethylaminopropylamino)-3,3,14-trimethyl-2,3,7,14-tetrahydro-1H-benzo[b]pyrano[3,2-h]acridin-7-one The procedure of Example 5 is followed, using the compound of Example 33 as substrate.

EXAMPLE 43 cis-1,2-Diacetoxy-6-[(2-morpholin-4yl)ethylamino]-3,3,14-trimethyl-2,3,7,14-tetrahydro-1H-benzo[b]pyrano[3,2-h]acridin-7-one The procedure of Example 5 is followed, using the compound of Example 34 as substrate.

EXAMPLE 44

(cis)-1,2-Diacetoxy-4-6-(2-piperidin-1-yl)ethylamino-3,3,14-trimethyl-2,3,7,14-tetrahydro-1H-benzo[b]pyrano[3,2-h]acridin-7-one The procedure of Example 5 is followed, using the compound of Example 35 as substrate

EXAMPLE 45

(trans)-1,2-Diacetoxy-6-(dimethylaminoethylamino)-3,3,14-trimethyl-2,3,7,14-tetrahydro-1H-benzo[b]pyrano[3,2-h]acridin-7-one The procedure of Example 5 is followed, using the compound of Example 36 as substrate.

EXAMPLE 46 cis-1,2-Diacetoxy-6-(dimethylaminoethyloxy)-3,3,14-trimethyl-2,3,7,14-tetrahydro-1H-benzo[b]pyrano[3,2-h]acridin-7-one The procedure of Example 5 is followed, using the compound of Example 37 as substrate.

EXAMPLE 47 cis-1,2-Diacetoxy-6-(dimethylaminopropyloxy)-3,3,
14-trimethyl-2,3,7,14-tetrahydro-1H-benzo[b]pyrano
[3,2-h]acridin-7-one The procedure of Example 5 is followed, using the compound of Example 38 as substrate.

EXAMPLE 48 cis-1,2-Diacetoxy-6-[(methoxycarbonyl)
methylamino]-3,3,14-trimethyl-2,3,7,14-tetrahydro-
1H-benzo[b]pyrano[3,2-h]acridin-7-one The procedure of Example 5 is followed, using the compound of Example 40 as substrate.

EXAMPLE 49 cis-1,2-Diacetoxy-6-[(methoxycarbonyl)
propylamino]-3,3,14-trimethyl-2,3,7,14-tetrahydro-
1H-benzo[b]pyrano[3,2-h]acridin-7-one The procedure of Example 5 is followed, using the compound of Example 41 as substrate.

EXAMPLE 50 cis-7-(Dimethylaminopropylamino)-4,4,15-
trimethyl-3a,8,15,15c-tetrahydro-4H-benzo[b][1,3]
dioxolo[4',5':4,5]pyrano[3,2-h]acridine-2,8-dione The procedure of Example 7 is followed, using the compound of Example 33 as substrate.

EXAMPLE 51 cis-6-[(2-Morpholin-4-yl)ethylamino]-4,4,15-
trimethyl-3a,8,15,15c-tetrahydro-4H-benzo[b][1,3]
dioxolo[4',5':4,5]pyrano[3,2-h]acridine-2,8-dione The procedure of Example 7 is followed, using the compound of Example 34 as substrate.

EXAMPLE 52 cis-6-[(2-Piperidin-1-yl)ethylamino]-4,4,15-
trimethyl-3a,8,15,15c-tetrahydro-4H-benzob[1,3]
dioxolo[4',5':4,5]pyrano[3,2-h]acridine-2,8-dione The procedure of Example 7 is followed, using the compound of Example 35 as substrate.

EXAMPLE 53 cis-6-(Dimethylaminoethyloxy)-4,4,15-trimethyl-3a,
8,15,15c-tetrahydro-4H-benzo[b][1,3]dioxolo[4',5':4,
5]pyrano[3,2-h]acridine-2,8-dione The procedure of Example 7 is followed, using the compound of Example 37 as substrate.

EXAMPLE 54 cis-6-[(Methoxycarbonyl)propylamino]-4,4,15-
trimethyl-3a,8,15,15c-tetrahydro-4H-benzo[b][1,3]
dioxolo[4',5':4,5]pyrano[3,2-h]acridine-2,8-dione The procedure of Example 7 is followed, using the compound of Example 41 as substrate.

EXAMPLE 55 cis-7-Methoxy-4,4,15-trimethyl-2-thioxo-3a,8,15,
15c-tetrahydro-4H-benzo[b][1,3]dioxolo[4',5':4,5]
pyrano[3,2-h]acridin-8-one The procedure of Example 7 is followed, using N,N'-thiocarbonyldiimidazole as reagent.

EXAMPLE 56 cis-7-(Dimethylaminoethylamino)-4,4,15-trimethyl-
2-thioxo-3a,8,15,15c-tetrahydro-4H-benzo[b][1,3]
dioxolo[4',5':4,5]pyrano[3,2-h]acridin-8-one The procedure of Example 55 is followed, using the compound of Example 15 as the substrate in the first step.

EXAMPLE 57

1,2-Diamino-6-methoxy-3,3,14-trimethyl-2,3,7,14-
tetrahydro-1H-benzo[b]pyrano[3,2-h]acridin-7-one The product is isolated by chromatography on silica gel starting from Example 22, where it is formed as co-product during the synthesis of that compound.

EXAMPLE 58

7-Methoxy-4,4,15-trimethyl-1,2,3,3a,4,8,15,15c-
octahydro-benzo[b]imidazo[4',5':4,5]pyrano[3,2-h]
acridine-2,8-dione The compound of Example 57 is treated according to the conditions described in *Tetrahedron Lett.* 1974, 1191.

EXAMPLE 59

7-Methoxy-4,4,15-trimethyl-2-thioxo-1,3a,4,8,15,
15c-hexahydro-2H-benzo[b][1,3]oxazolo[4',5':4,5]
pyrano[3,2-h]acridin-8-one The procedure of Example 55 is followed, using the compound of Example 22 as substrate.

EXAMPLE 60

9-Methoxy-6,6,17-trimethyl-1,3,4,5a,6,10,17,17c-
octahydro-2H-benzo[b][1,4]oxazepino[3',2':4,5]
pyrano[3,2-h]acridine-2,4,10-trione The procedure of Example 16 is followed, using the compound of Example 22 as substrate.

EXAMPLE 61

10,11-Dichloro-6-hydroxy-3,3-dimethyl-7,14-
dihydro-3H-benzo[b]pyrano[3,2-h]acridin-7-one The procedure of Example 1, Steps A and B, is followed, using 3-amino-6,7-dichloro-2-naphthalenecarboxylic acid as substrate in Step A.

EXAMPLE 62

10,11-Dichloro-6-methoxy-3,3,14-trimethyl-7,14-
dihydro-3H-benzo[b]pyrano[3,2-h]acridin-7-one The procedure of Example 2 is followed, using the compound of Example 61 as substrate.

EXAMPLE 63 cis-10,11-Dichloro-1,2-dihydroxy-6-methoxy-3,3,
14-trimethyl-2,3,7,14-tetrahydro-1H-benzo[b]pyrano
[3,2-h]acridin-7-one The procedure of Example 4 is followed, using the compound of Example 62 as substrate.

EXAMPLE 64

6-Hydroxy-9,12-dimethoxy-3,3-dimethyl-7,14-
dihydro-3H-benzo[b]pyrano[3,2-h]acridin-7-one The procedure of Example 1, Steps A and B, is followed, using 3-amino-5,8-dimethoxynaphthalenecarboxylic acid as substrate in Step A.

EXAMPLE 65

6,9,12-Trimethoxy-3,3,14-trimethyl-7,14-dihydro-3H-benzo[b]pyrano[3,2-h]acridin-7-one The procedure of Example 2 is followed, using the compound of Example 64 as substrate.

EXAMPLE 66

10,11-Di-tert-butyl-4-hydroxy-3,3-dimethyl-7,14-dihydro-3H-benzo[b]pyrano[3,2-h]acridin-7-one The procedure of Example 1, Steps A and B, is followed, using 3-amino-6,7-di-tert-butyl-naphthalenecarboxylic acid as substrate in Step A

EXAMPLE 67

10,11-Di-tert-butyl-6-methoxy-3,3,14-trimethyl-7,14-dihydro-3H-benzo[b]pyrano[3,2-h]acridin-7-one The procedure of Example 2 is followed, using the compound of Example 66 as substrate.

EXAMPLE 68 cis-10,11-Di-tert-butyl-1,2-dihydroxy-6-methoxy-3,3,14-trimethyl-2,3,7,14-tetrahydro-1H-benzo[b]pyrano[3,2-h]acridin-7-one The procedure of Example 4 is followed, using the compound of Example 67 as substrate.

EXAMPLE 69 cis-1,2-Diacetoxy-10,11-di-tert-butyl-6-methoxy-3,3,14-trimethyl-2,3,7,14-tetrahydro-1H-benzo[b]pyrano[3,2-h]acridin-7-one The procedure of Example 5 is followed, using the compound of Example 68 as substrate.

EXAMPLE 70

10,11-Di-tert-butyl-(dimethylaminoethylamino)-3,3,14-trimethyl-7,14-dihydro-3H-benzo[b]pyrano[3,2-h]acridin-7-one The procedure of Example 8 is followed, using the compound of Example 67 as substrate.

Pharmacological Study of Compounds of the Invention

EXAMPLE 71

In vitro Activity

Murine leukaemia L1210 was used in vitro. The cells are cultured in RPMI 1640 complete culture medium containing 10% foetal calf serum, 2 mM giutamine, 50 units/ml of penicillin, 50 μg/ml of streptomycin and 10 mM Hepes, pH: 7.4. The cells are distributed on microplates and exposed to the cytotoxic compounds for 4 periods of cell doubling, i.e. 48 hours. The number of viable cells is then quantified by means of a colorimetric assay, the Microculture Tetrazolium Assay (J. Carmichael et al., *Cancer Res.*, 47, 936–942, (1987)). The results are expressed as $IC_{50}$, the concentration of cytotoxic agent which inhibits the proliferation of the treated cells by 50%. The results obtained are shown in Table 1.

TABLE 1

Cytotoxicity for L1210 cells in culture

| Products | Cytotoxicity $IC_{50}$ (μM) |
| --- | --- |
| Example 7 | 0.023 |
| Acronycine | 27.0 |

All the compounds of the invention are more potent than the refaence compound acronycine.

EXAMPLE 72

In vivo Activity

1-Anti-tumour Activity on Line P 388

Line P 388 (murine leukaemia) was supplied by the National Cancer Institute (Frederick, USA). The tumour cells ($10^6$ cells) were inoculated on day 0 into the peritoneal cavity of female B6D2F1 mice (Iffa Credo, France). Six mice weighing from 18 to 20 g were used for each experimental group. The products were administered by the intraperitoneal route on day 1.

The anti-tumour activity is expressed as % TIC:

$$\% \, T/C \, (\text{survival}) = \frac{\text{Median survival time of the treated animals}}{\text{Median survival time of the control animals}} \times 100$$

Table 2 shows the anti-tumour activity obtained at the optimum doses.

TABLE 2

Anti-tumour activity on line P 388

| Product | Schedule | Route | Optimum dose (mg/kg) | % T/C |
| --- | --- | --- | --- | --- |
| Example 7 | d1 | i.p. | 12.5 | 327 |
| Acronycine | d1 | i.p. | 200 | 125 |

The product of Example 7 is very active in this model, while acronycine is only marginally active.

2-Anti-tumour Activity on Human Colon Carcinoma HT29

Line HT29 was supplied by the ATCC (American Type Culture Collection, Rockville, USA). The tumour cells were inoculated into female nude Swiss mice ($10^7$ cells per animal) by the subcutaneous route. The tumours were then removed and cut into fragments, which were grafted onto nude mice by the subcutaneous route. Once the tumour volume had reached from 50 to 100 $mm^3$, the mice were distributed into experimental groups containing 8 animals (control group) or 6 animals (treated groups) (day 0). The products were administered by the i.v. route once per week for 3 weeks. The tumours were measured twice per week and the tumour volumes were calculated according to the formula: volume ($mm^3$)=length (mm)×width$^2$ ($m^2$)/2

The results are expressed as % $T/C$ =

$$\frac{\text{median} \, (Vt/V0) \, \text{of the treated group}}{\text{median} \, (Vt/V0) \, \text{of the control group}} \times 100$$

with V0 and Vt being the initial volume and the volume at measurement time t, respectively.

Table 3 shows the anti-tumour activity obtained at the optimum doses for the compound of Example 5.

TABLE 3

Anti-tumour activity on line HT29

| Product | Schedule | Route | Optimum dose (mg/kg) | % T/C on day 32 |
|---|---|---|---|---|
| Example 5 | d 0, 7, 14 | i.v. | 3.12 | 17 |

The compound of Example 5 inhibits the growth of the HT29 tumour, which is generally not very sensitive to anti-tumour agents. The compound is very active in this model, with inhibition being 83% on day 32, i.e. 18 days after the first administration.

EXAMPLE 73

Pharmaceutical Composition: Tablets

Preparation formula for 1000 tablets each containing 10 mg:

| | |
|---|---|
| compound of Example 7 | 10 g |
| lactose | 40 g |
| magnesium stearate | 10 g |
| wheat starch | 15 g |
| cornstarch | 15 g |
| silica | 3 g |
| hydroxypropyl cellulose | 5 g |

What is claimed is:

1. A compound selected from those of formula (I):

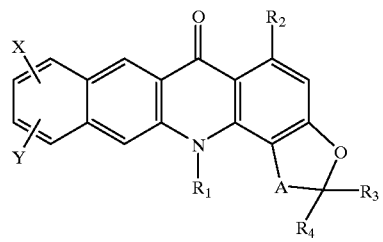

in which

X and Y, which may be identical or different, each independently of the other represents a group selected from hydrogen, halogen, hydroxy, mercapto, cyano, nitro, linear or branched $(C_1-C_6)$alkyl, linear or branched $(C_1-C_6)$alkoxy, linear or branched $(C_1-C_6)$ trihaloalkyl, and amino which is optionally substituted by one or two, identical or different, linear or branched $(C_1-C_6)$alkyl which are themselves optionally substituted by linear or branched $(C_1-C_6)$alkoxy or by —$NR_7R_8$ wherein $R_7$ and $R_8$, which may be identical or different, each independently of the other represents hydrogen or linear or branched $(C_1-C_6)$alkyl, or X and Y together form methylenedioxy or ethylenedioxy, $R_1$ represents hydrogen or linear or branched $(C_1-C_6)$ alkyl, $R_2$ represents a group selected from:
hydrogen,
hydroxy,
linear or branched $(C_1-C_6)$alkyl,
linear or branched $(C_1-C_6)$alkoxy which is optionally substituted:

by $NR'_7R'_8$ wherein $R'_7$ and $R'_8$, which may be identical or different, each independently of the other represent a group selected from hydrogen, linear or branched $(C_1-C_6)$alkyl, and linear or branched $(C_1-C_6)$hydroxyalkyl, or by a saturated or unsaturated, monocyclic or bicyclic heterocycle having 5 to 7 ring members, and containing one or two hetero atoms selected from oxygen, nitrogen, and sulphur, linear or branched $(C_1-C_6)$alkylcarbonyloxy, and amino which is optionally substituted:
by one or two, identical or different, linear or branched $(C_1-C_6)$alkyl,
by linear or branched $(C_1-C_6)$alkylcarbonyl which is optionally substituted by —$NR'_7R'_8$ wherein $R'_7$ and $R'_8$ are as defined above,
by —$R_9$—$NR'_7R'_8$ wherein $R_9$ represents linear or branched $(C_1-C_6)$alkylene and $R'_7$ and $R'_8$, which may be identical or different, each independently of the other represents a group selected from hydrogen, linear or branched $(C_1-C_6)$alkyl, and linear or branched $(C_1-C_6)$hydroxyalkyl,
by linear or branched $(C_1-C_6)$alkylene which is substituted by a saturated or unsaturated, monocyclic or bicyclic heterocycle having 5 to 7 ring members and containing one or two hetero atoms selected from oxygen, nitrogen, and sulphur,
or by

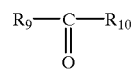

wherein $R_9$ is as defined above, and $R_{10}$ represents hydroxy or linear or branched $(C_1-C_6)$alkoxy, $R_3$ and $R_4$, which may be identical or different, each independently of the other represents hydrogen or linear or branched $(C_1-C_6)$alkyl, A represents —CH=CH—, or ethylene with the formula —CH($R_5$)—CH($R_6$) wherein $R_5$ and $R_6$, which may be identical or different, each independently of the other represents:
hydrogen,
hydroxy,
linear or branched $(C_1-C_6)$alkoxy,
linear or branched $(C_1-C_6)$alkylcarbonyloxy,
arylcarbonyloxy,
amino optionally substituted by one or two, identical or different, linear or branched $(C_1-C_6)$alkyl, or linear or branched $(C_1-C_6)$acyl,
mercapto, linear or branched $(C_1-C_6)$alkylthio, or arylthio, or $R_5$ and $R_6$ together form:

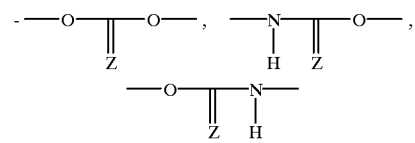

wherein Z represents oxygen or sulphur,

—O—(CH₂)ₙ—O— wherein n is 1 to 4 inclusibve,

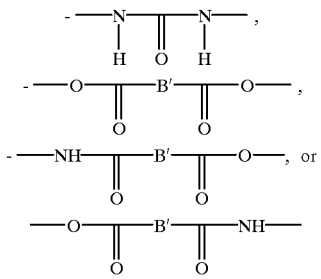

(C₁–C₆)alkylene or linear (C₂–C₆)alkylene, or R₅ and R₆ form, together with the carbons carrying them, oxirane or azirideine, optionally substituted on nitrogen by linear or branched (C₁–C₆)alkyl, wherein the term "aryl" denotes phenyl or naphthyl, optionally containing one or more, identical or different, substituents selected from hydroxy, halogen, carboxy, nitro, amino, linear or branched (C₁–C₆)alkylamino, linear or branched di-(C₁–C₆)alkylamino, linear or branched (C₁–C₆)alkoxy, linear or branched (C₁–C₆)acyl, and linear or branched (C₁–C₆)alkylcarbonyloxy, its optical isomers, diastereomers, N-oxides, and pharmaceutically-acceptable acid or base addition salts thereof.

2. A compound of claim 1, wherein R₃ and R₄, which may be identical or different, represent linear or branched (C₁–C₆)alkyl.

3. A compound of claim 1, wherein that R₂ represents linear or branched (C₁14 C₆)alkoxy, or amino which is optionally substituted 4. A compound of claim 1, wherein R₂ represents amino substituted by —R₉—NR₇R₈ wherein R₉ represents linear or branched (C₁–C₆)alkylene, and R₇ and R₈, which may be identical or different, represent hydrogen or linear or branched (C₁–C₆)alkyl, its isomers, N-oxides, and pharmaceutically-acceptable acid or base addition salts thereof.

5. A compound of claim 1, wherein A represents —CH=CH—, or —CH(R₅)—CH(R₆)— wherein R₅ and R₆ represent hydroxy, linear or branched (C₁₋₆) alkylcarbonyloxy, or R₅ and R₆ together form

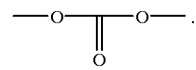

6. A compound of claim 1 which is (±)-cis-1,2diacetoxy-&methoxy-3,3,14-trimethyl-2,3,7,14-tetrahydro-1H-benzo[b]pymano[3,2-h]-acridin-7-one.

7. A compound of claim 1 which is cis-7-methoxy-4,4,15-trimethyl-3a,8,15,15c-tetrahydro-4H-benzo[b][1,3]dioxolo[4',5':4,5]pyrano[3,2-h]acridine-2,8dione.

8. A compound of claim 1 which is 6-methoxy-3,3,14-trimethyl-7,14-dihydro-3H-benzo[b]pyrano[3,2-h]acridin-7-one.

9. A compound of claim 1 which is 6-(diethylaminopropylamino)-3,3,14-trimethyl-7,14-dihydro-3H-benzo[b]pyrano[3,2-h]acridin-7-one.

10. A compound of claim 1 which is (±)-cis-diacetoxy-6-(diethylaminopropylamino)-3,3,14-trimethyl-2,3,7,14-tetrahydro-1H-benzofpyrano[3,2-h]acridin-7-one.

11. A method for treating a living body afflicted with a cancer susceptible to treatment with acronycine, comprising the step of administering to the living body in need thereof an amount of a compound of claim 1 which is effective for alleviation of said cancer.

12. A pharmaceutical composition comprising compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO.   : 6,288,073 B1
DATED        : September 11, 2001
INVENTOR(S)  : Michel Koch et al.

Page 1 of 1

It is certified that error appears in the above-identified patent and that said Letters Patent is hereby corrected as shown below:

Column 29,
Line 56, "$_{and\ R8}$" should read -- and $R_8$ --.

Column 31,
Line 1, "inclusibve," should read -- inclusive, --
Line 14, please insert before " $(C_1 - C_6)$ alkylene " the following text; -- wherein B represents a single bond, linear --
Line 33, "14" should be -- - --.

Column 32,
Line 27 "benzofpyrano" should read -- benxof[b]pyrano --

Signed and Sealed this

Fourteenth Day of May, 2002

Attest:

*Attesting Officer*

JAMES E. ROGAN
*Director of the United States Patent and Trademark Office*